United States Patent

Khanna et al.

[11] Patent Number: 5,869,649
[45] Date of Patent: Feb. 9, 1999

[54] PROCESS FOR PRODUCING CEPHALOSPORIN ANTIBIOTICS

[75] Inventors: Jag Mohan Khanna; Vijay Kumar Handa; Ramesh Dandala; Ram Chander Aryan, all of New Delhi, India

[73] Assignee: Ranbaxy Laboratories Ltd., New Delhi, India

[21] Appl. No.: 641,954

[22] Filed: May 1, 1996

[30] Foreign Application Priority Data

Mar. 18, 1996 [IN] India .................................. 560/Del/96

[51] Int. Cl.⁶ .................................................. C07D 501/06
[52] U.S. Cl. ............................................. 540/227; 540/228
[58] Field of Search ..................... 540/227, 228

[56] References Cited

U.S. PATENT DOCUMENTS

| | | | |
|---|---|---|---|
| 4,767,852 | 8/1988 | Ascher | 540/222 |
| 5,026,843 | 6/1991 | Riccardo | 540/227 |
| 5,527,906 | 6/1996 | Milac et al. | 540/227 |
| 5,574,154 | 11/1996 | Abu-Nasrieh | 540/227 |
| 5,583,216 | 12/1996 | Ochiai et al. | 540/222 |
| 5,607,927 | 3/1997 | Tsushima et al. | 540/227 |

OTHER PUBLICATIONS

Organic Chemistry, Cram & Hammand, 2nd Ed (1964) McGraw Hill Book Co, N.Y.

Tetrahedron Letters, 31, 6481 (1980), Author Donald G. Walker.

Primary Examiner—John M. Ford
Attorney, Agent, or Firm—Proskauer Rose LLP

[57] ABSTRACT

A process for preparing certain cephalosporin antibiotics, namely, cefotaxime, cefetemet, and ceftriaxone sodium comprising acylation of 7-amino-3-cephem-4-carboxylic acid derivatives with 2-mercapto-5-methyl-1,3,4-thiadiazolyl-(Z)-2-(2-aminothiazol-4-yl)-2-methoxyiminoacetate having the formula:

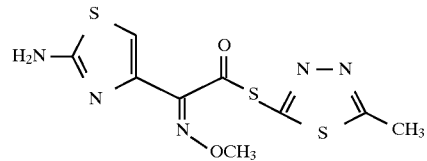

14 Claims, No Drawings

PROCESS FOR PRODUCING CEPHALOSPORIN ANTIBIOTICS

BACKGROUND OF THE INVENTION

The present invention relates to a new process for the preparation of antibiotic substances belonging to the cephalosporin class of compounds. More specifically, the present invention relates to a new process for the preparation of cefotaxime, cefetamet, and ceftriaxone sodium. The latter compounds belong to a known class of valuable cephalosporanic antibiotics disclosed, for example, in U.S. Pat. No. 4,098,888 (1978) as well as numerous other patents and other publications. This class of antibiotics is characterized by the presence of an oximino group and a 2-aminothiazolyl heterocyclic ring in the 7-acylamido side-chain attached to the cephalosporin nucleus. This class of compounds is also characterized by suitable substituents at the 3-position of the cephalosporin nucleus. It is known that the oximino group in the 7-acylamido side-chain may have the syn or anti configuration, but that the syn isomers have higher antibiotic activity. See, e.g., U.S. Pat. No. 4,152,432 (1979) and U.S. Pat. No. 4,224,371 (1980).

Conventionally, this class of compounds is prepared by first introducing the suitable substituent into the 3-position of the cephalosporin nucleus, and then attaching the suitable substituent to the nitrogen in the 7-position. Thus, U.S. Pat. No. 4,767,852 (1988) discloses a process for the production of known 2-oximinoacetamido-3-cephem-4-carboxylic acid derivatives, including cefotaxime and ceftriaxone, by acylating 7-amino-3-cephem-4-carboxylic acid derivatives already substituted at the 3-position with 2-mercaptobenzothiazolyl-(Z)-2-(2-aminothiazol-4-yl)-2-methoxyiminoacetate, the latter often being referred to as MAEM. Similarly, U.S. Pat. No. 5,026,843 (1991) discloses a process for preparing ceftriaxone disodium salt hemiheptahydrate. As the first step in the process disclosed in that patent, 7-aminocephalosporanic acid (7-ACA) already suitably substituted at the 3-position is acylated at the 7-position using MAEM as the acylating agent. Thus, MAEM has become the standard acylating agent for the preparation of cephalosporins having an oximino group and a 2-aminothioazolyl group in the 7-acylamido side-chain.

However, there are certain disadvantages to using MAEM as the acylating agent. In particular, a by-product of this reaction is the toxic compound 2-mercaptobenzothiazole. See, e.g., *Chemical Abstracts* 111, 19243 p (1989). Therefore, there has been an ongoing search for new acylating agents which are capable of introducing the 2-aminothiazolyl group as part of the 7-acylamido side-chain in good yield, but without producing this toxic by-product.

In *Tetrahedron Letters* 31, 6481 (1990), Walker, D. G., reports the use of certain thioesters, including 2-mercapto-5-methyl-1,3,4-thiadiazolyl-(Z)-2-(2)-tritylaminothiazol-4-yl)-2-methoxyiminoacetate and 2-mercapto-5-methyl-1,3,4-thiadiazolyl-(Z)-2-(2-aminothiazol-4-yl)-2-methoxyiminoacetate, as acylating agents in the synthesis of cefepime sulfate. Yields are reported to be in the range of 54–73% when using the latter thioester, which are far below the yields of 85–97% reported for the production of cefotaxime and ceftriaxone when using MAEM as the acylating agent. See, e.g., Examples 1 and 3 of U.S. Pat. No. 4,767,852 and the Example of U.S. Pat. No. 5,026,843.

SUMMARY AND DETAILED DESCRIPTION OF THE INVENTION

In accordance with the present invention, there is provided a new process for producing cephalosporin antibiotics, specifically cefotaxime, cefetamet and ceftriaxone sodium of high purity and in good yield.

According to the present invention syn isomers of the formula I

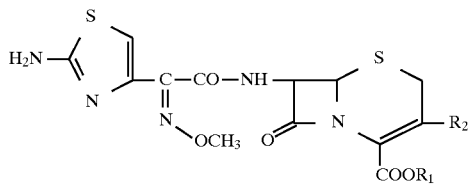

in which
R$_1$ is hydrogen or a carboxy protecting group such as pivaloyloxymethyl, and
R$_2$ is acetoxymethyl, methyl, or (2,5-dihydro-6-hydroxy-2-methyl-5-oxo-1,2,4-triazin-3-yl)thiomethyl, or a pharmaceutically acceptable salt form thereof are prepared by reacting 2-mercapto-5-methyl-1,3,4-thiadiazolyl-(Z)-2-(2-aminothiazol-4-yl)-2-methoxyiminoacetate of formula II

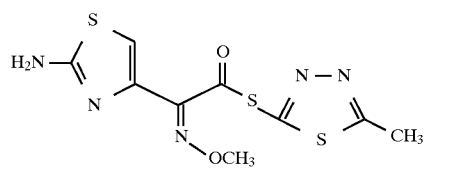

with cephalosporins of formula III

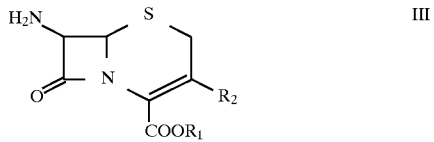

in which R$_1$ and R$_2$ are as defined above.

Particularly preferred compounds produced by the inventive process are syn isomers having the formula Ia

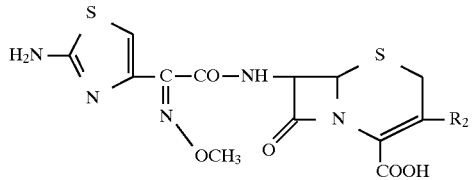

in which
R$_2$ is acetoxymethyl (cefotaxime),
R$_2$ is methyl (cefetamet), or
R$_2$ is (2,5-dihydro-6-hydroxy-2-methyl-5-oxo-1,2,4-triazin-3-yl)thiomethyl (ceftriaxone).

The present invention provides a method by which the syn isomers of the previously mentioned cephalosporins may be obtained in high purity and in good yield without the necessity for protecting the amino group of the acylating agent. Additionally, yields are comparable to those obtained when using MAEM as the acylating agent, but without the production of the toxic by-product 2-mercaptobenzothiazole.

The cephalosporins produced by the present process are of great therapeutical interest due to their effective antibacterial activity and are useful in the treatment of several infections.

The process is suitably carried out in an aqueous medium at a temperature of −5° to +20° C. in the presence of suitable organic solvents, such as, tetrahydrofuran, N,N-dimethylacetamide, N,N-dimethylformamide, dioxane, and suitable mixtures thereof, or in an inert organic solvent, such as, chlorinated hydrocarbons, ethyl acetate or ether. Preferably, the reaction is carried out in the presence of tetrahydrofuran and N,N-dimethylacetamide. Desirably, the reaction is also carried out in the presence of a tertiary amine such as triethylamine, N-methylpiperidine, pyridine, 1,8-diazabicycloundecene, N-methylmorpholine, 4-dimethylaminopyridine, or mixtures thereof.

The following examples illustrate the inventive process.

EXAMPLE 1

3-Acetoxymethyl-7-[(Z)-2-(2-aminothiazol-4-yl)-2-(methoxyimino)acetamido]-3-cephem-4-carboxylic acid (Cefotaxime).

A mixture of tetrahydrofuran (89 ml), water (89 ml) and N,N-dimethylacetamide (14 ml) was stirred under nitrogen atmosphere and at 0°–5° C., 7-aminocephalosporanic acid (8.16 g) was added followed by 2-mercapto-5-methyl-1,3,4-thiadiozolyl-(Z)-2-(2-aminothiazol-4-yl)-2-methoxyimino acetate (11.34 g). Triethylamine was added to the stirred reaction mixture to maintain the pH between 7–8. The gradual disappearance of 7-aminocephalosporanic acid was monitored using HPLC. After 3 hours of stirring, the reaction mixture was extracted with methylene chloride and the aqueous layer was treated with activated carbon. Isopropyl alcohol (75 ml) was then added to the filtrate and the contents were acidified at 0°–5° C. with 2N HCl to pH 2.8–3.0. The resulting precipitate was filtered and washed successively with water and isopropyl alcohol, and then dried under reduced pressure to obtain cefotaxime of high purity.

Yield: 13.3 gm (97.5% of theoretical yield)

EXAMPLE 2

3-Methyl-7-[(Z)-2-(2-aminothiazol-4-yl)-2-(methoxyimino)acetamido]-3-cephem-4-carboxylic acid (Cefetamet).

A mixture of tetrahydrofuran (238 ml), water (200 ml) and N,N-dimethylacetamide (30 ml) was cooled to 0°–10° C. under nitrogen atmosphere. 7-Amino-3-desacetoxycephalosporanic acid (21.7 g) was added followed by 2-mercapto-5-methyl-1,3,4-thiadiazolyl-(Z)-2-(2-aminothiazol-4-yl)-2-methoxyimino acetate (37.8 g). Triethylamine was added to maintain the pH between 6.8–8.5 and when the amount of 7-amino-3-desacetoxycephalosporanic acid was less than 0.5%, water was added. The pH was adjusted to 6.0–6.4 by adding a few drops of acetic acid. Methylene chloride was then added. The aqueous layer was separated, acidified to pH 2.8–3.5 with 2N HCl (at 3°–5° C.), and the resulting precipitate was filtered. It was dried under reduced pressure at 40° C. to obtain 35.7 g of cefetamet of 99% purity.

Yield: 35.7 g (88.5% of theoretical yield)

EXAMPLE 3

7-[[2-(2-Aminothiazol-4-yl)-2-syn-methoxyimino]acetamido]-3-[[2,5-dihydro-6-hydroxy-2-methyl-5-oxo-1,2,4-triazin-3-yl)thio]methyl]-3-cephem-4-carboxylic acid disodium salt hemiheptahydrate (Ceftriaxone sodium).

To a solution of tetrahydrofuran (56 ml), water (29.68 ml), and N,N-dimethylacetamide (11.87 ml) at 0°–5° C., under nitrogen atmosphere, 7-amino-3-[[(2,5-dihydro-6-hydroxy-2-methyl-5-oxo-1,2,4-triazin-3-yl)thio]methyl]-3-cephem-4-carboxylic acid (7.42 g) was added followed by 2-mercapto-5-methyl-1,3,4-thiadiazolyl-(Z)-2-(2-aminothiazol-4-yl)-2-methoxyimino acetate (7.56 g). Triethylamine (4.04 g) was added and the mixture was stirred at 18°–20° C. while maintaining the pH between 7–8 for 3 to 4 hours. Methylene chloride was added and the aqueous layer was separated. Thereafter, a solution of sodium 2-ethylhexanoate (11.62 g) in acetone was added to the aqueous layer at 18°–20° C. and the reaction mixture was stirred for 1 hour to get crystals of ceftriaxone sodium. More acetone was added slowly to complete crystallization and the product was filtered and washed with acetone. The product thus obtained was dried under reduced pressure to give substantially pure ceftriaxone sodium.

Yield: 12 g (90% of theoretical yield)

EXAMPLE 4

3-Acetoxymethyl-7-[(Z)-2-(2-aminothiazol-4-yl)-2-(methoxyimino)acetamido]-3-cephem-4-carboxylic acid (Cefotaxime)

2,2'-Dithio-bis-5-methyl-1,3,4-thiadiazole (48.09 g) and (Z)-2-(2-aminothiazol-4-yl)-2-methoxyiminoacetic acid (23.38 g) were suspended in tetrahydrofuran (297 ml) and triphenylphosphine (48.09) was added at 20°–25° C. This mixture was stirred for half an hour to generate 2-mercapto-5-methyl-1,3,4-thiadiazolyl-(Z)-2-(2-aminothiazol-4-yl)-2-methoxyimino acetate in solution. Thereafter, the reaction mixture was cooled to 3°–5° C., diluted with N,N-dimethylacetamide (46.8 ml), water (297 ml) and 7-aminocephalosporanic acid (27.2 g) was added, followed by triethylamine addition in 20 min. The reaction was continued for 3–4 hours at 3°–5° C. Thereafter, acetic acid (18 g) and water (100 ml) were added and the aqueous layer was thoroughly extracted with methylene chloride to remove tetrahydrofuran and other by-products. The aqueous phase containing triethylamine salt of cefotaxime acid was mixed with excess isopropyl alcohol (250 ml) and acidified to pH 2.80 at 0°–5°° C. with hydrochloric acid to precipitate cefotaxime acid. The mixture was then filtered, the solids washed with water, isopropyl alcohol and dried to obtain cefotaxime acid.

Yield: 42 g (92% of theoretical yield)

While the invention has been described by reference to specific examples, this was for purposes of illustration only. Numerous alternative embodiments will be apparent to those skilled in the art and were considered to be within the scope of the invention.

We claim:

1. A process for preparing a compound of formula I

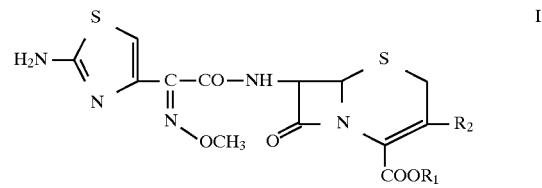

wherein $R_1$ represents hydrogen or a carboxy protecting group, and $R_2$ represents acetoxymethyl, methyl, or (2,5-dihydro-6-hydroxy-2-methyl-5-oxo-1,2,4-triazin-3-yl)thiomethyl, or a pharmaceutically acceptable salt form thereof, which comprises acylating a compound of formula III

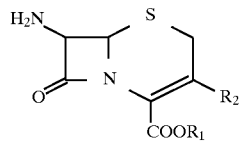

in which $R_1$ and $R_2$ are as defined above,
with a compound of formula II

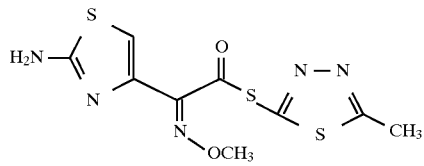

2. The process of claim 1 wherein $R_2$ is acetoxymethyl.

3. The process of claim 1 wherein $R_2$ is methyl.

4. The process of claim 1 wherein $R_2$ is (2,5-dihydro-6-hydroxy-2-methyl-5-oxo-1,2,4-triazin-3-yl)thiomethyl.

5. The process of claim 1 wherein $R_1$ is hydrogen.

6. The process of claim 1 wherein $R_1$ is an alkali metal salt.

7. The process of claim 1 wherein $R_1$ is pivaloyloxymethyl.

8. The process of claim 1 wherein said compound of formula I is a syn isomer.

9. The process of claim 1 wherein said acylation is performed in the presence of an organic solvent and water.

10. The process of claim 1 wherein said organic solvent is selected from the group consisting of tetrahydrofuran, N,N-dimethylacetamide, N,N-dimethylformamide, dioxane, and mixtures thereof.

11. The process of claim 1 wherein said acylation is performed in the presence of an organic base.

12. The process of claim 1 wherein said organic base is selected from the group consisting of triethylamine, N-methylmorpholine, pyridine, 1,8-diazabicycloundecene, and 4-dimethylaminopyridine, and mixtures thereof.

13. The process of claim 1 wherein said acylation is carried out at a temperature in the range of $-5°$ to $+20°$ C.

14. The process of claim 1 wherein said compound of formula II is produced in situ.

* * * * *